(12) United States Patent
Anthony et al.

(10) Patent No.: US 7,163,551 B2
(45) Date of Patent: Jan. 16, 2007

(54) SURGICAL STAPLING DEVICE

(76) Inventors: Thomas Anthony, 49 Grange Downs, Rathfarnham, Dublin 14 (IE); Christy Cummins, 9 Furnes Manor, Johnstown, Nass, County Kildare (IE); Paul Hooi, 105 Brodford Hill, Ballinteer, Dublin 16 (IE)

( * ) Notice: Subject to any disclaimer, the term of this patent is extended or adjusted under 35 U.S.C. 154(b) by 192 days.

(21) Appl. No.: 10/486,067

(22) PCT Filed: Aug. 8, 2002

(86) PCT No.: PCT/IE02/00119

§ 371 (c)(1),
(2), (4) Date: Feb. 6, 2004

(87) PCT Pub. No.: WO03/013364

PCT Pub. Date: Feb. 20, 2003

(65) Prior Publication Data

US 2004/0236355 A1 Nov. 25, 2004

(30) Foreign Application Priority Data

Aug. 9, 2001 (IE) ............................. S2001/0749

(51) Int. Cl.
*A61B 17/04* (2006.01)

(52) U.S. Cl. .................. 606/219; 606/213; 606/216; 227/175.01; 227/176.01

(58) Field of Classification Search ............... 606/219, 606/215, 213, 216, 142, 143, 151, 139; 227/19, 227/175.1, 180.1, 175.01, 180.01

See application file for complete search history.

(56) References Cited

U.S. PATENT DOCUMENTS

| 3,482,428 | A | 12/1969 | Kapitanov et al. |
| 4,014,492 | A | 3/1977 | Rothfuss |
| 4,523,695 | A | 6/1985 | Braun et al. |
| 4,724,840 | A | 2/1988 | McVay et al. |
| 4,771,782 | A | 9/1988 | Millar |
| 4,789,090 | A | 12/1988 | Blake, III |
| 4,934,364 | A | 6/1990 | Green |
| 5,108,421 | A | 4/1992 | Fowler |
| 5,131,379 | A | 7/1992 | Sewell, Jr. |

(Continued)

FOREIGN PATENT DOCUMENTS

EP 0 386 361 9/1990

(Continued)

*Primary Examiner*—(Jackie) Tan-Uyen Ho
*Assistant Examiner*—Natalie Pous
(74) *Attorney, Agent, or Firm*—Nutter, McClennen & Fish LLP

(57) ABSTRACT

A surgical stapling device is provided having a shaft, a surgical staple slidable longitudinally within the shaft, and a staple-firing mechanism for driving the staple towards the forward end of the housing, bending the staple to bring the free ends of the legs towards one another to close the staple, and releasing the closed staple. The device also includes a blood locator tube slidable longitudinally within the shaft between an initial extended position wherein a forward end of the tube projects beyond the forward end of the shaft to enter a puncture site in a liquid-carrying vessel in a human or animal, thereby to locate the forward end of the shaft at the puncture site, and a retracted position wherein the tube is retracted into the housing in coordination with the closure of the staple. The tube has a longitudinal slot extending rearwardly from its forward end and the back of the staple is accommodated transversely in the slot.

5 Claims, 4 Drawing Sheets

U.S. PATENT DOCUMENTS

| | | |
|---|---|---|
| 5,147,381 A | 9/1992 | Heimerl et al. |
| 5,192,300 A | 3/1993 | Fowler |
| 5,275,616 A | 1/1994 | Fowler |
| 5,292,309 A | 3/1994 | Van Tassel et al. |
| 5,292,332 A | 3/1994 | Lee |
| 5,306,254 A | 4/1994 | Nash et al. |
| 5,395,030 A | 3/1995 | Kuramoto et al. |
| 5,431,639 A | 7/1995 | Shaw |
| 5,443,481 A | 8/1995 | Lee |
| 5,470,010 A | 11/1995 | Rothfuss et al. |
| 5,478,352 A | 12/1995 | Fowler |
| 5,527,322 A | 6/1996 | Klein et al. |
| 5,536,251 A | 7/1996 | Evard et al. |
| 5,560,532 A | 10/1996 | DeFonzo et al. |
| 5,591,205 A | 1/1997 | Fowler |
| 5,601,602 A | 2/1997 | Fowler |
| 5,620,461 A | 4/1997 | Muijs Van De Moer et al. |
| 5,643,318 A | 7/1997 | Tsukernik et al. |
| 5,645,566 A | 7/1997 | Brenneman et al. |
| 5,674,231 A | 10/1997 | Green et al. |
| 5,676,689 A | 10/1997 | Kensey et al. |
| 5,716,375 A | 2/1998 | Fowler |
| 5,725,554 A * | 3/1998 | Simon et al. ............... 606/219 |
| 5,810,846 A * | 9/1998 | Virnich et al. .............. 606/142 |
| 5,855,312 A | 1/1999 | Toledano |
| 5,861,005 A | 1/1999 | Kontos |
| 6,004,341 A | 12/1999 | Zhu et al. |
| 6,007,563 A | 12/1999 | Nash et al. |
| 6,022,372 A | 2/2000 | Kontos |
| 6,048,358 A | 4/2000 | Barak |
| 6,056,768 A | 5/2000 | Cates et al. |
| 6,090,130 A | 7/2000 | Nash et al. |
| 6,197,042 B1 | 3/2001 | Ginn et al. |
| 6,277,140 B1 | 8/2001 | Ginn et al. |
| 6,322,580 B1 | 11/2001 | Kanner |
| 6,348,064 B1 | 2/2002 | Kanner |
| 6,506,210 B1 | 1/2003 | Kanner |
| 6,533,762 B1 | 3/2003 | Kanner et al. |
| 6,623,510 B1 | 9/2003 | Carley et al. |
| 6,719,777 B1 | 4/2004 | Ginn et al. |
| 6,755,842 B1 | 6/2004 | Kanner et al. |
| 6,767,356 B1 | 7/2004 | Kanner et al. |
| 2002/0049472 A1 | 4/2002 | Coleman |
| 2002/0151921 A1 | 10/2002 | Kanner et al. |
| 2003/0097140 A1 | 5/2003 | Kanner |
| 2003/0109890 A1 | 6/2003 | Kanner et al. |
| 2004/0010285 A1 | 1/2004 | Carley et al. |
| 2004/0254591 A1 | 12/2004 | Kanner et al. |
| 2004/0267312 A1 | 12/2004 | Kanner et al. |

FOREIGN PATENT DOCUMENTS

| | | |
|---|---|---|
| EP | 0 534 696 | 3/1993 |
| EP | 0 756 851 | 2/1997 |
| EP | 0 774 237 | 5/1997 |
| EP | 0 941 697 | 9/1999 |
| FR | 2 443 238 | 7/1980 |
| GB | 1 358 466 | 7/1974 |
| WO | WO 97/20505 | 6/1997 |
| WO | WO 98/17179 | 4/1998 |
| WO | WO 98/25508 | 6/1998 |
| WO | WO 00/56227 | 9/2000 |

* cited by examiner

SURGICAL STAPLING DEVICE

CROSS-REFERENCE TO RELATED APPLICATIONS

This application is the U.S. national stage application of International Application No. PCT/IE02100119, filed Aug. 8, 2002, entitled "Surgical Stapling Device," which designated the United States and was in the English language, and which claims priority to Ireland Application No. S200110749, filed Aug. 9, 2001, entitled "Surgical Stapling Device." These applications are expressly incorporated by reference herein.

FIELD OF THE INVENTION

This invention relates to a surgical stapling device.

BACKGROUND OF THE INVENTION

Surgical stapling devices have been in existence for many years. They are routinely used in surgical procedures mainly for the purposes of effecting a wound closure. Some of the most popular applications include closing a skin incision and end-to-end or end-to-side anastomosis of internal (generally tubular) vessels such as the large bowel, etc. Current staplers are designed to deliver one or more staples in a serial fashion or a number of staples in one shot. Skin staplers, for example, deliver 30 or more staples in a serial fashion. The staples are stacked within the device and during the firing operation one staple is advanced from the stack and delivered through the head of the device. During the following cycle another staple is advanced from the top of the stack and again delivered through the head of the device and so on. In one shot devices such as a bowel anastomosis stapler the staples are prearranged in a linear or circular fashion and upon activation of the device all the staples are delivered through the head. Examples of existing prior art as described above include U.S. Pat. Nos. 4,592,498, 5,289,963, 5,433,721 and 5,470,010.

The mechanism involved in forming a staple and releasing it from its forming mechanism is common to the majority of surgical stapler devices. Generally the components include an anvil, a staple closing actuator, and a staple release mechanism. The anvil is normally positioned in front of the staple and the actuator directly behind the staple. As the actuator advances the staple against the anvil the back section of the staple deforms around both ends of the anvil thereby transforming the staple from a generally U-shape to a generally rectangular shape. At this point the actuator generally retracts and the staple is released from the anvil either as a result of the anvil moving out of position and allowing the staple to move forward, or alternatively ejecting the staple over the anvil thereby releasing it from the device.

A mechanism such as that described above, used in conjunction with a blood location tube, is described in Irish Patent Application S2000/0722. This describes a stapling device which has a generally oval cross-section blood locator tube that protrudes ahead of the device. The function of the blood locator tube is to track down over a guidewire through the tissue and into the opening in the artery. Once in the artery, blood flows back up one side of the locator tube and exits the device outside the body where the operator can see it. This indicates to the operator that the device is in place and it is safe to operate. This patent application also describes a specially designed staple (humpback staple) which wraps around the locator tube so that it can be deployed centrally across the radial opening in the artery. The benefits of using an oval locator tube and a humpback staple are that the staple is located centrally in the artery and hence the staple used need not be so large, and in turn, the dimensions of the shaft, which must accommodate the staple when in its unformed state, can be reduced, leading to less trauma to the tissue into which the shaft is introduced. A further consequence of having a generally oval or elongated cross section for the locator tube is that the tube will be more disposed to the center of the puncture than with a rounded tube. The device has a staple that straddles the locator tube, thereby increasing the likelihood of the staple closing the elongated wound at its center rather than towards one or other of the extremities of the wound.

The above device using a humpback staple has a number of disadvantages. When compared to conventional straight backed staples it can be appreciated that as the staple is formed around the anvil, the back is placed under tension, tending to cause the hump to collapse. In addition, because of the presence of the blood locator tube the anvil is reduced to individual fingers which tend to collapse inward due to lack of central support.

Furthermore, because of the position of the locator tube the staple former must be generally U-shaped in section so as to straddle it. Because of this the working fingers have a tendency to spread outward during the forming process.

It is an object of the invention to provide an improved surgical stapling device in which these disadvantages are avoided or mitigated, while retaining the benefits of centrally positioning the staple across the radial tear.

SUMMARY OF THE INVENTION

The present invention provides a surgical stapling device that generally includes an elongate housing having a free forward end, a surgical staple slidable longitudinally within the housing towards the forward end thereof and having a back and two forwardly pointing legs, a staple-firing mechanism for driving the staple towards the forward end of the housing, bending the staple to bring the free ends of the legs towards one another to close the staple, and releasing the closed staple, and an elongated locator member slidable longitudinally within the housing between an initial extended position wherein a forward end of the locator member projects beyond the forward end of the housing to enter a puncture site in a liquid-carrying vessel in a human or animal, thereby to locate the forward end of the housing at the puncture site, and a retracted position wherein the locator member is retracted into the housing in coordination with the closure of the staple. The locator member can also include a longitudinal slot extending rearwardly from its forward end partially along the length of the locator member. The slot allows the back of the staple to be accommodated transversely therein with its forwardly pointing legs disposed externally of and respectively on opposite sides of the locator member.

BRIEF DESCRIPTION OF THE DRAWINGS

This object is achieved by the invention claimed in the appended claims.

An embodiment of the invention will now be described, by way of example, with reference to the accompanying drawings, in which.

DETAILED DESCRIPTION OF THE PRESENT INVENTION

Figure 1:
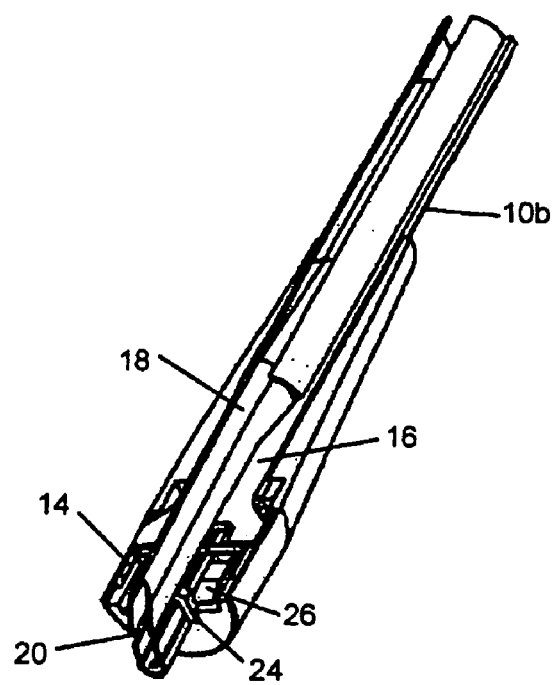
FIG. 1 is a perspective view of the forward end of an embodiment of a surgical stapling device according to the invention.
Figure 2:
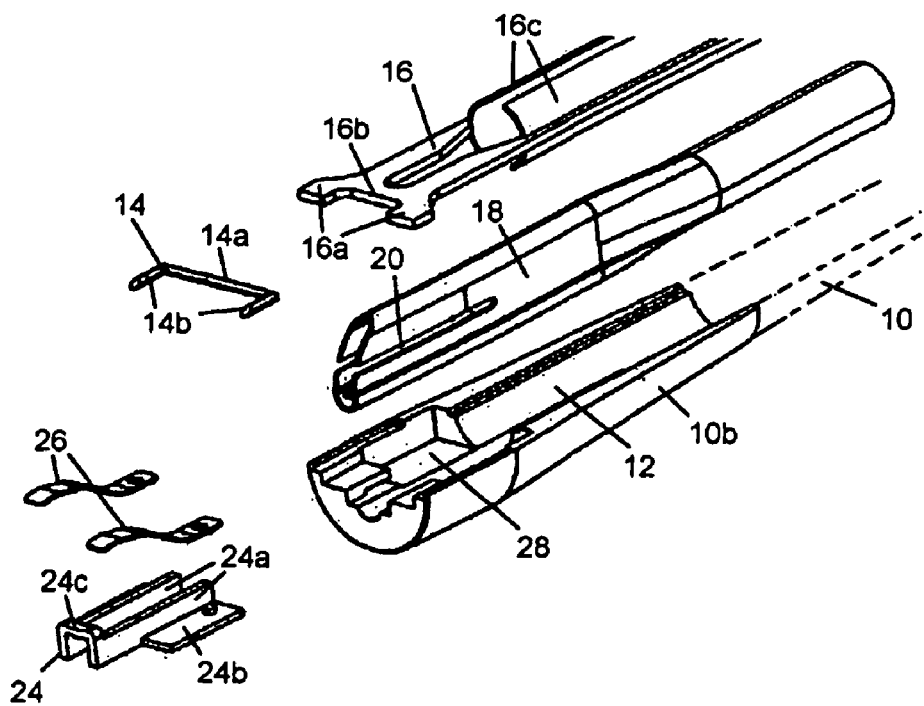
FIG. 2 shows the device of FIG. 1 in exploded view.
Figure 3:
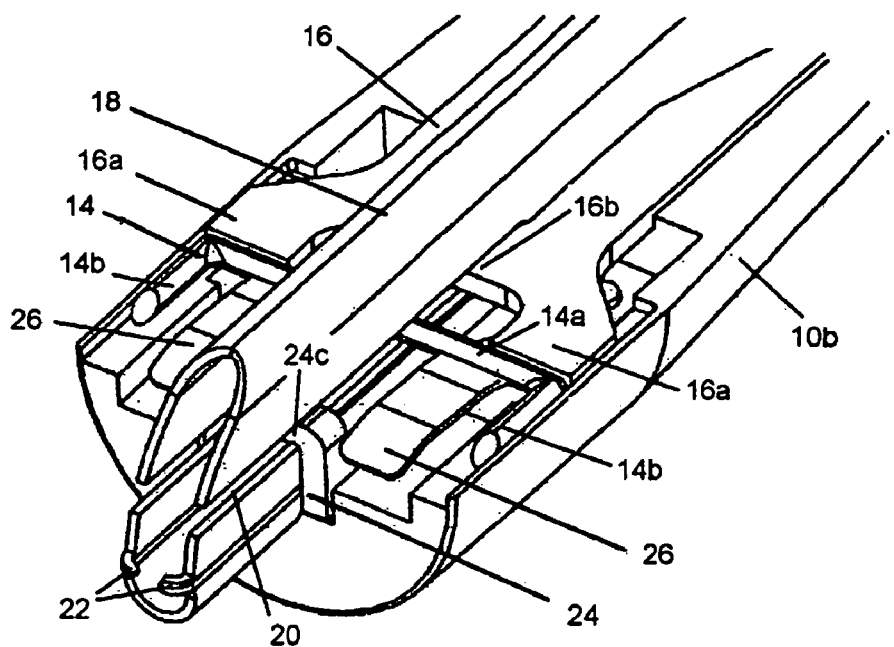
FIGS. 3 to 6 are perspective views of the device of FIG. 1 at successive stages of operation in firing a staple.

Referring initially to FIGS. 1 to 3, a surgical stapling device comprises an elongated housing or shaft 10 having upper and lower halves 10a and 10b defining between them a longitudinal channel 12 for slidably accommodating a staple 14, a staple closing actuator 16 and a blood locator tube 18. (Only the lower housing half 10b is shown in FIGS. 1 to 6 to reveal the internal components. Also, only the free forward end of the housing 10 is shown in the drawings, since that is where the invention lies in the present embodiment.) The rear end of the housing 10 is preferably formed with a pistol grip and the movement of the various components to be described may be effected by a trigger acting through a cam system. Such an arrangement is described in Irish Patent Application S2000/0722 which may be readily adapted to operate the device of the present embodiment.

The blood locator tube 18 is, except for a longitudinal slot 20, of substantially the same construction as that described in Irish Patent Application S2000/0722. Thus it has a generally oval cross-section at the distal end and is slidable longitudinally within the housing 10 between an initial extended position (FIG. 3) wherein a forward end of the tube 18 projects beyond the forward end of the housing to enter a puncture site in a liquid-carrying vessel in a human or animal, thereby to locate the forward end of the housing at the puncture site, and a retracted position (FIG. 6) wherein the tube 18 is retracted into the housing in coordination with the closure of the staple.

The tube 18 serves two purposes. In use it is tracked along a guidewire (not shown) to bring the front end of the housing 10 to the site of a puncture wound, and it allows blood to flow back along the housing to the handle to permit the operator to see when the forward end of the housing has penetrated the wound. This is as described in Irish Patent Application S2000/0722. However, in the present embodiment the tube 18 has a longitudinal slot 20 extending rearwardly from its forward end partially along the length of the locator member. In this embodiment the slot 20 is about 5 mm long. A pair of inwardly bent tabs 22 at the front end of the tube 18 confine the guidewire to the region of the tube below the slot 20 (referring to the orientation seen in the drawings), to avoid the guidewire interfering with the movement of the staple and actuator within the slot, to be described.

The actuator 16 is an elongated member having a forward end which is forked to provide two arms 16a connected by a transverse bridge 16b. The bridge 16b extends transversely through the slot 20 with the arms 16a extending forwardly on either side of the tube 18. The rear of the actuator 16 comprises a pair of opposed part-cylindrical shells 16c which slidably embrace the tube 18 to allow the actuator 16 to slide longitudinally thereon.

The staple 14 is a standard, generally U-shaped staple having a straight back 14a and two forwardly pointing legs 14b. The free ends of the staple legs 14b are sharpened for ease of tissue penetration. In use of the device the back 14a of the staple is accommodated transversely in the slot 20 with its forwardly pointing legs 14b disposed externally of and respectively on opposite sides of the tube 18.

The device further includes an anvil 24. This is made out of stamped and bent metal sheet and comprises a pair of opposite parallel side plates 24a each with a laterally extending wing 24b, and a bridge element 24c joining the font ends of the side plates 24a. In use of the device the anvil 24 is fixed by its wings 24b in a recess 26 in lower housing half 18b with the side plates 24a disposed respectively on opposite sides of the tube 18 and the bridge element 24c extending transversely through the slot 20 in front of the staple 14. The bridge element 24c is substantially flush with the front surface of the housing 10. Finally, a pair of staple ejection springs 28 have their rear ends fixed respectively to the wings 24b and their free front ends, when unrestrained, extending upwardly above the level of the bridge element 24c.

The operation of the device will now be described with reference to FIGS. 3 to 6.

In the initial configuration of the device, FIG. 3, the tube 18 is in its extended position wherein the forward end of the tube 18 projects beyond the forward end of the housing 10. The actuator 16 is retracted rearwardly and an undeformed staple 14 sits freely in the slot 20 just ahead of the arms 16a. The anvil bridge element 24c is in the slot 20 spaced ahead of the staple back 14a and flush with the front surface of the housing 10. All components are held in position by the top housing half 10a not shown in FIGS. 3 to 6.

Figure 4:
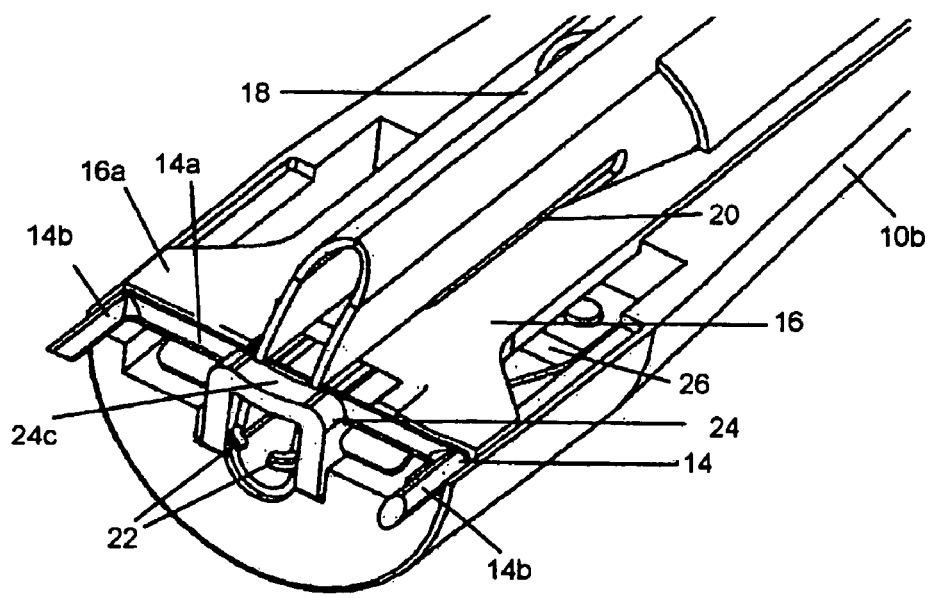

Upon operation of the trigger previously mentioned, or other operating mechanism, the actuator 16 is driven forwardly towards the free forward end of the housing 10. This drives the staple 14 before it by engagement of the actuator arms 16a with the outer portions of the staple back 14a. During such forward movement the staple deflects the free ends of the ejection springs 28 downwardly. At the same time the blood locator tube 18 starts to be retracted in coordination with the movement of the staple. FIG. 4 shows the positions of the components just as the back 14a of the staple reaches the fixed anvil bridge element 24c.

Deformation of the staple is about to take place at this stage.

Figure 5:
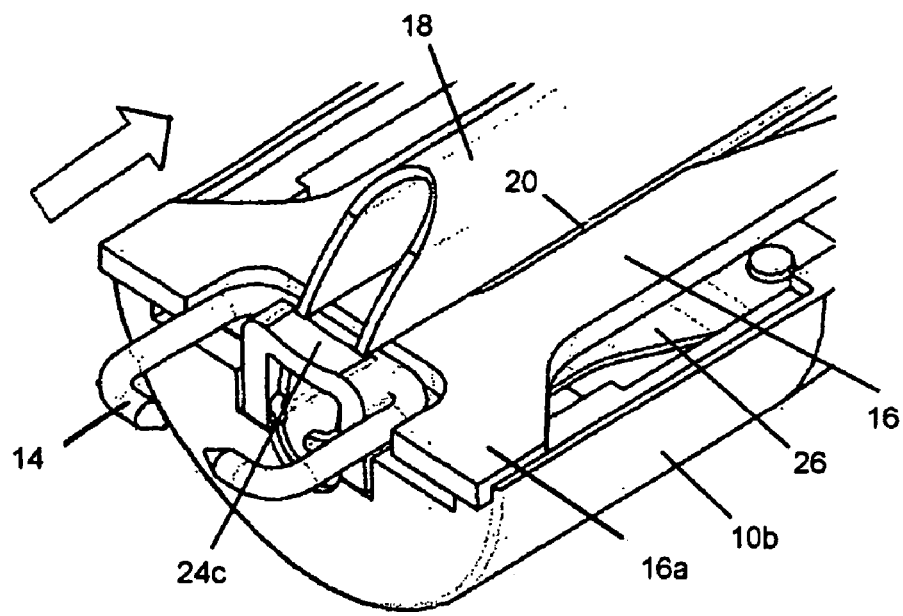

Upon further forward movement of the actuator 16, FIG. 5, the staple is deformed around the anvil bridge element 24c, thereby bending the staple to bring the free ends of the legs 14b towards one another to close the staple in a generally rectangular shape.

Figure 6:
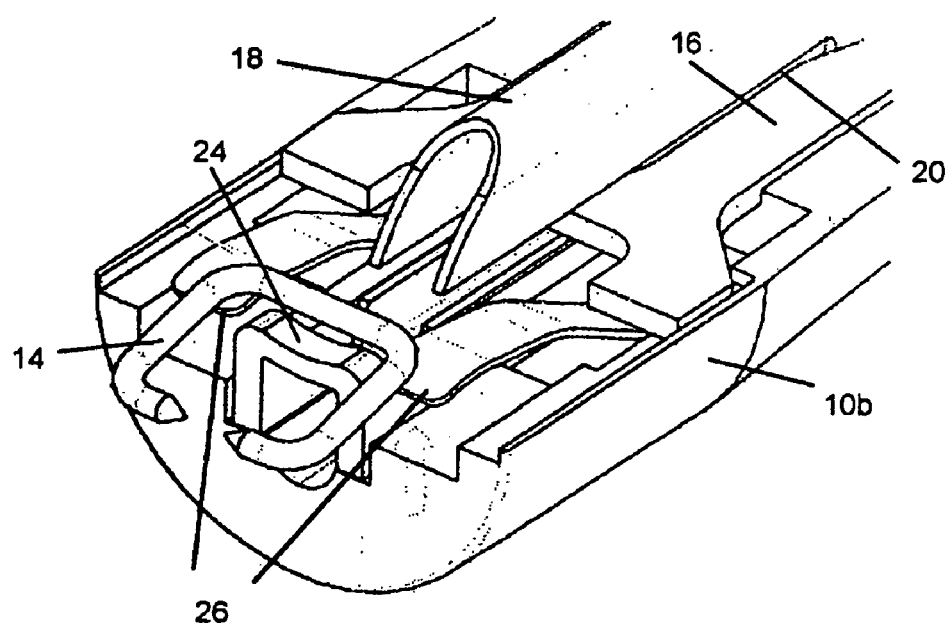
Figure 7:
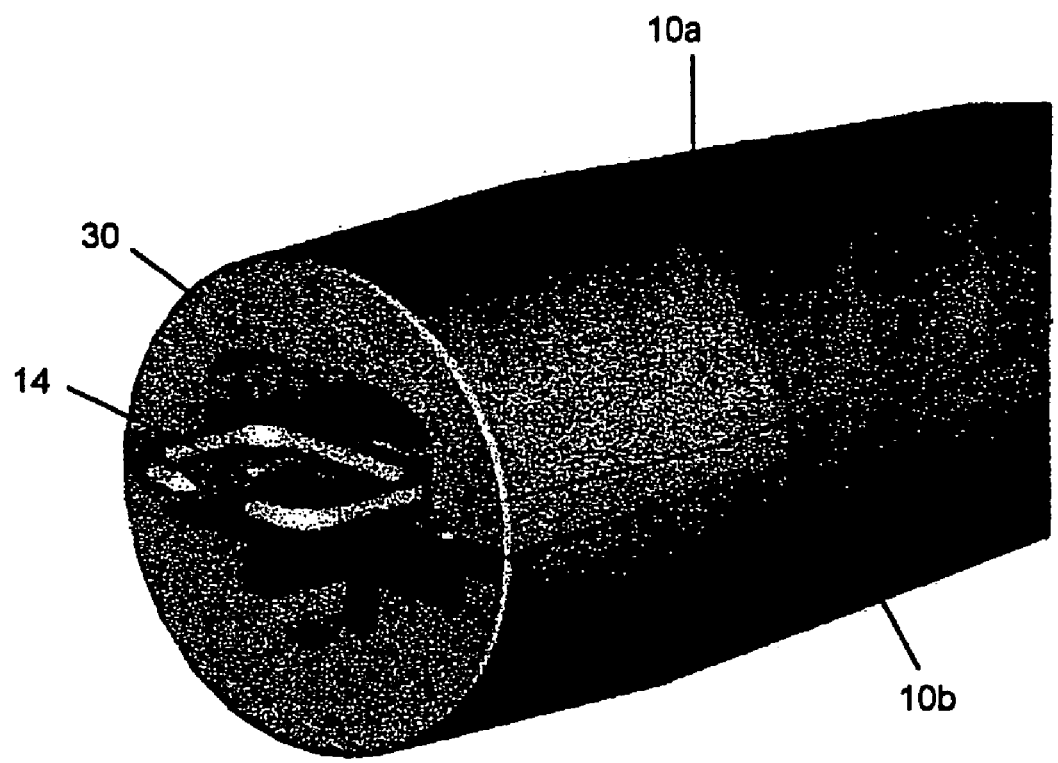
FIG. 7 is a perspective view of the device at the point of staple release.

Finally, FIG. 6, further retraction of the blood locator tube 18 clears the closed staple 14 to allow the ejection springs 28 to push the closed staple upwardly relative to the transverse bridge element 24c to release the staple. As seen in FIG. 7, the upper housing half 10a has a recess 30 at its front end to allow this upward movement of the closed staple.

The benefits of the foregoing embodiment over the device described in Irish Patent Application S2000/0722 are:

a. A standard straight legged staple can be used. This will deform in a more predictable manner, it is less expensive to manufacture and is less likely to become caught in the anvil or shaft.

b. As the staple used is straight there is less risk that the staple will open up and create a "lazy" staple effect.

c. A larger blood locator tube can be used for ease of manufacture and increased blood flow for better indication of position.

d. Stronger and easier to manufacture anvil due to the transverse bridge.

e. Bridge between forming components of former to prevent spreading during the staple forming process.

Also it is possible to define a configuration which incorporates not one but two staples. Both staples would be located in respective slots on either side of the blood locator tube. A configuration such as this allows for the passage of a component such as a guidewire between both staples that would facilitate the process of blindly locating puncture holes in vessels.

The invention is not limited to the embodiment described herein and may be modified or varied without departing from the scope of the invention.

The invention claimed is:

1. A surgical stapling device, comprising:
an elongate housing having a free forward end;
a surgical staple slidable longitudinally within the housing towards the forward end thereof, the staple having a back and two forwardly pointing legs;
a staple-firing mechanism for driving the staple towards the forward end of the housing, bending the staple to bring the free ends of the legs towards one another to close the staple, and releasing the closed staple; and
an elongated locator member slidable longitudinally within the housing between an initial extended position wherein a forward end of the locator member projects beyond the forward end of the housing to enter a puncture site in a liquid-carrying vessel in a human or animal, thereby to locate the forward end of the housing at the puncture site, and a retracted position wherein the locator member is retracted into the housing in coordination with the closure of the staple, wherein the locator member has a longitudinal slot extending rearwardly from its forward end partially along the length of the locator member, and wherein the back of the staple is accommodated transversely in the slot with its forwardly pointing legs disposed externally of and respectively on opposite sides of the locator member.

2. A device as claimed in claim 1, wherein the staple-firing mechanism comprises an actuator slidable longitudinally of the housing within the slot for driving the staple towards the forward end of the housing, and an anvil against which the staple is driven by the actuator to deform and close the staple.

3. A device as claimed in claim 2, wherein the anvil comprises an element extending transversely through the slot in the locator member in front of the staple, the forward end of the locator member being positioned behind the said transverse member in the retracted position of the locator member to allow release of the closed staple.

4. A device as claimed in claim 3, further including resilient biasing means for pushing the closed staple upwardly relative to the transverse element to release the closed staple.

5. A device as claimed in claim 1, wherein the locator member comprises a hollow tube for accommodating a guidewire and for conducting blood back along the housing to a visualization port.

* * * * *